United States Patent [19]

Buelna

[11] Patent Number: 5,242,409
[45] Date of Patent: Sep. 7, 1993

[54] FLEXIBLE ACCESS DEVICE

[75] Inventor: Terrence J. Buelna, Rancho Santa Margarita, Calif.

[73] Assignee: Applied Medical Resources Corporation, Laguna Hills, Calif.

[21] Appl. No.: 701,207

[22] Filed: May 16, 1991

[51] Int. Cl.⁵ .............................................. A61M 5/00
[52] U.S. Cl. ................................... 604/164; 606/191
[58] Field of Search ............... 606/191; 604/41, 164, 604/171, 261, 264, 275, 277; 128/207.14, 207.29, 200.22

[56] References Cited

U.S. PATENT DOCUMENTS 3,606,669  9/1971  Kemble ........................ 128/200.26
4,331,138  5/1982  Jessen ................................ 606/185
4,654,030  3/1987  Moll .
4,716,901  1/1988  Jackson et al. ................. 128/200.26
4,976,684  12/1990 Broadnax, Jr. .

Primary Examiner—C. Fred Rosenbaum
Assistant Examiner—W. Lewis
Attorney, Agent, or Firm—Richard L. Myers

[57] ABSTRACT

An access device is adapted to facilitate introduction into a body cavity, such as the abdominal cavity, of an instrument having an elongate shaft and a bend in the shaft. The device includes a hub having a wall disposed at the proximal end of a cannula which is configured to extend into the cavity. The hub has a normal configuration with a length and diameter which inhibits passage of the bend of the shaft through the hub, but the wall of the hub is progressively bendable from the normal configuration to facilitate passage of the bend through the hub.

11 Claims, 2 Drawing Sheets

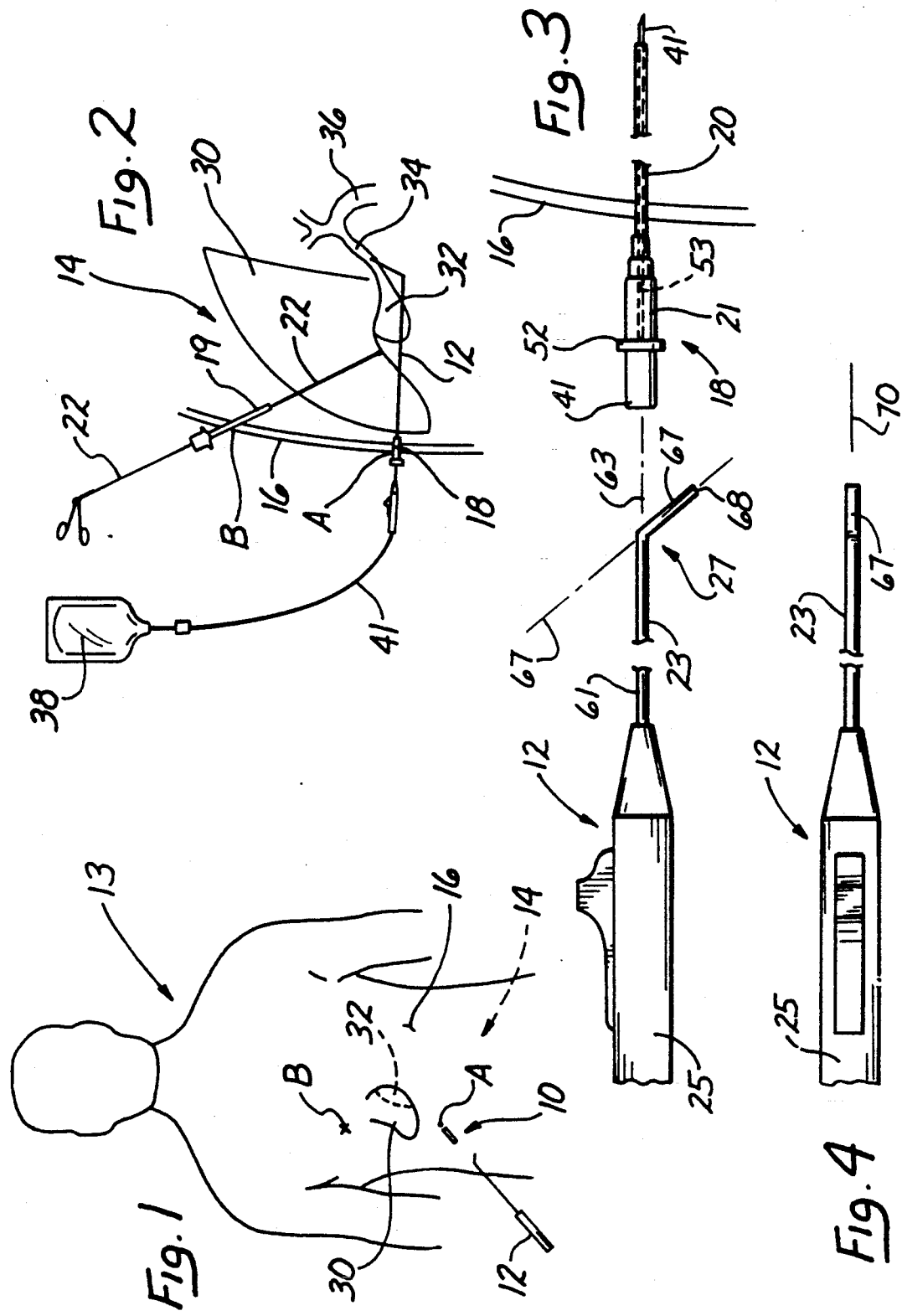

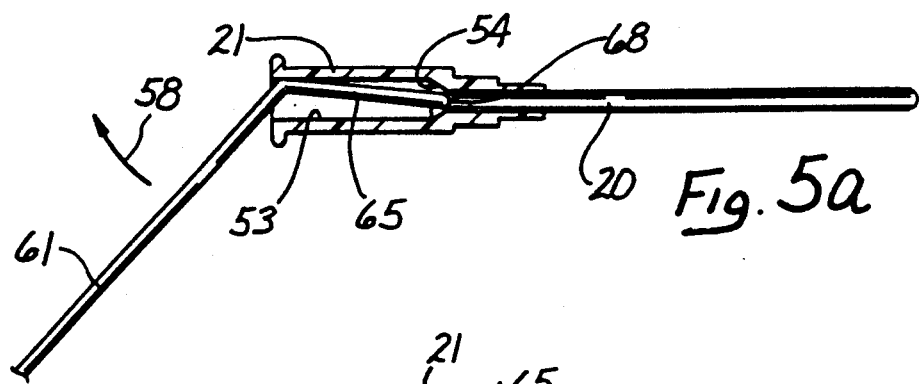
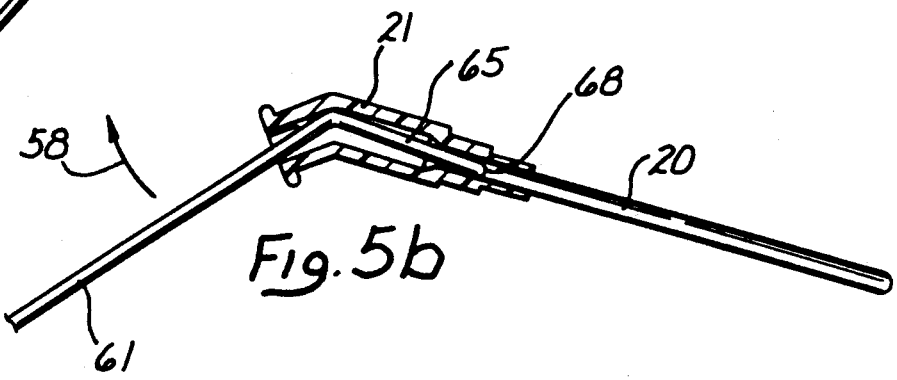
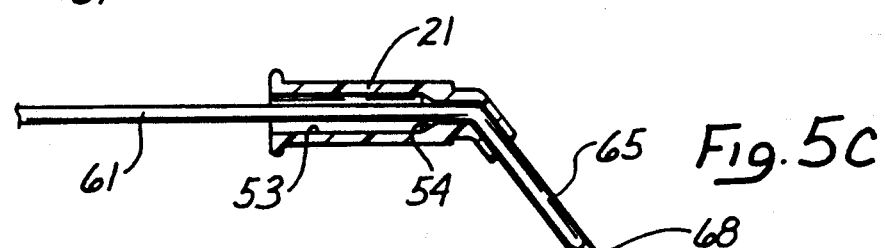
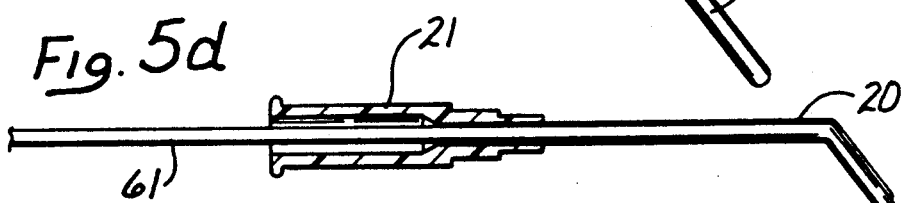
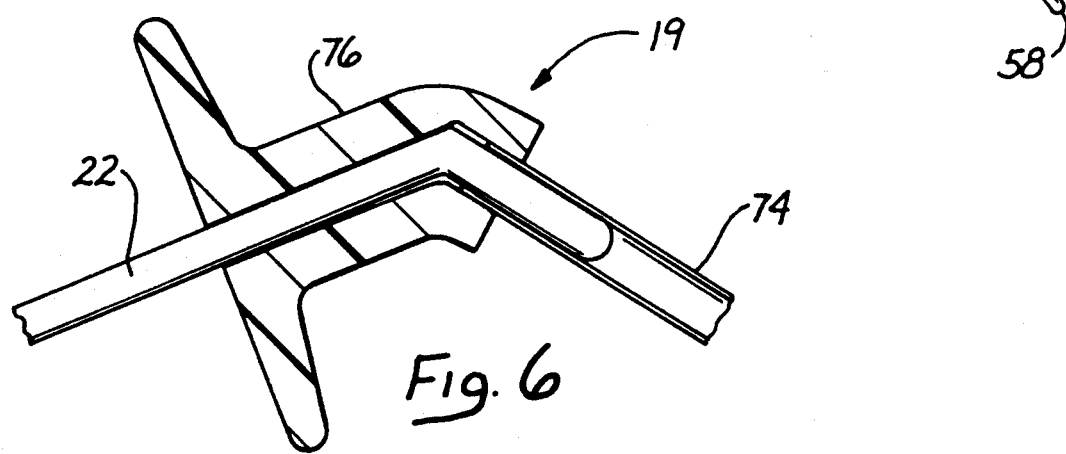

FLEXIBLE ACCESS DEVICE

BACKGROUND OF THE INVENTION

1. Field of the Invention

This invention relates generally to trocars, introducers and other access devices which are insertible percutaneously to facilitate introduction of a catheter or other instrument into a body conduit or cavity.

2. Discussion of the Prior Art

As methods are being developed to accomplish surgical procedures with less invasive techniques, instruments which are adapted for use in those procedures are also evolving. Many procedures concerning the organs in the abdominal cavity are now being accomplished through small holes in the abdominal wall. These procedures, collectively referred to as laparoscopy, are far less traumatic to the patient, greatly reduce infection rates, and significantly decrease recovery time.

Instruments adapted for use in laparoscopic procedures are typically inserted through the abdominal wall using special access devices such as introducers and trocars. These devices generally include an elongate cannula extending to a distal end of the device and a hub disposed at a proximal end of the device. A needle or obturator is initially disposed through the channel of the access device and is used to puncture the abdominal wall. As the needle is inserted it carries the cannula of the device into its operative position. Then the needle is removed leaving the cannula in place across the abdominal wall.

Access devices have been sized to provide a channel which is only slightly larger than the diameter of the instrument which is intended for insertion through the device. In the case of introducers, the cannula of the device has been formed from a flexible material and provided with a length such as three inches. The hubs of the introducers have been made from a rigid plastic material and provided with a length such as three-quarter inches.

For years, instrument designers have accepted the limitations of such access devices and created their instruments with only straight shafts or tubes. This has not only limited the design possibilities for the instruments, but also greatly increased the difficulties encountered in using such instruments.

It is now apparent that many surgical procedures can be greatly facilitated by providing instruments with a bend which will enable the surgeon to manipulate the instrument through a particular insertion site and into a particular location. Such an instrument cannot be introduced through the access devices of the prior art.

Although the cannula of the access devices have been flexible and capable of passing the bend in the shaft of an instrument, the rigid hub has made the passage of bent instruments totally impossible. In some cases, surgeons have been required to insert the access device and then cut the hub from the cannula. This leaves only the flexible cannula in place thereby permitting the introduction of a bent shaft. However, one of the purposes of the hub is to provide an enlarged structure exteriorly of the body which will prevent the cannula from falling into the cavity. If the surgeon is forced to remove the enlarged hub, this risk of contamination becomes a dramatic possibility.

SUMMARY OF THE INVENTION

In accordance with the present invention, an access device is provided with structural characteristics which can accommodate the introduction of an instrument having a bent configuration. This will permit many variations to be made in the design of surgical instruments. An example of such an instrument is the catheter disclosed and claimed in applicant's co-pending application, Ser. No. 664,067, filed on Mar. 1, 1991, and entitled Cholangiography Catheter. This instrument includes a shaft which is approximately twelve inches in total length and is provided with a bend of 45×approximately one and one-half inches from the distal end of the catheter.

In one aspect, the invention includes the combination of an elongate surgical instrument and an access device facilitating introduction of the instrument into the body of a patient. A shaft included in the instrument is disposed along an elongate axis which includes a bend such as 30×. A cannula and hub form the access device, the hub having a rigid configuration and defining a passage having a narrow axial dimension and a diameter sufficiently large to pass the bend of the instrument.

In another aspect of the invention, an access device is adapted to facilitate introduction of an instrument into a body cavity, the instrument having an elongate shaft and a bend in the shaft. The device includes a cannula and a hub disposed at the proximal end of the cannula. The hub is characterized by walls having an inner surface with a length and a diameter. In a normal configuration of the hub, the length and diameter are insufficient to pass the bend of the shaft through the hub. However, the hub is progressively bendable along the axis of the bore to permit passage of the bend through the hub.

In a preferred method, the invention includes the steps of inserting the shaft of the instrument into the hub up to the bend in the shaft, and bending the hub to facilitate passage of the bend in the shaft through the hub.

Thus, in accordance with the concepts of the present invention, surgical laparoscopic instruments can be provided with significant bends along their length which are not restricted by the structural characteristics of the associated access devices. These devices can be provided with narrow rigid hubs facilitating the passage of such bent instruments. In the alternative, the hubs of the access devices can be provided with flexible characteristics enabling the bend of the instrument to be progressively forced through the hub of the access device.

These and other features of the present invention will become more apparent with a description of preferred embodiments and reference to the associated drawings.

DESCRIPTION OF THE DRAWINGS

FIG. 1 is a schematic view of a human body illustrating abdominal characteristics which may be of interest to a particular laparoscopic procedure;

FIG. 2 is a side-elevation view of the abdominal area of a patient illustrating devices and procedures associated with a cholangiography procedure;

FIG. 3 is an assembly view illustrating an access device and a bent catheter forming a combination of the present invention;

FIG. 4 is a top plan view of the bent catheter illustrated in FIG. 3;

FIG. 5a–5d illustrate the steps in a preferred method for inserting a bent instrument through an access device of the present invention;

FIG. 5a is a side elevation view of the instrument showing a bend in the shaft of the instrument as it enters a hub of the access device;

FIG. 5b is a side elevation view showing the instrument bend within the flexible hub of the access device;

FIG. 5c is a side elevation view showing the instrument bend as it passes from the hub into a cannula of the access device;

FIG. 5d is a side elevation view showing the instrument bend in the cannula of the access device; and FIG. 6 is a side elevation view of a bent instrument moving through a flexible housing and cannula of a trocar.

DESCRIPTION OF PREFERRED EMBODIMENTS

An access device is illustrated in FIGS. 1 and 2 and designated generally by the reference numeral 10. The device 10 is particularly adapted for introducing a surgical instrument such as a cholangiography catheter 12 from outside the body of a patient 13 into a particular body passage or cavity, such as the abdominal cavity 14. This introduction of the catheter 12 through the access device 10 typically takes place across a barrier such as the abdominal wall 16.

The access device 10 is representative of both introducers, such as an introducer 18, and trocars, such as the trocar 19. Both of these devices include a cannula 20 and a hub 21. In the case of the introducer 18, the cannula 20 may have a relatively small size such as 7 Fr. which is suitable for introducing smaller instruments such as the catheter 12. In the case of the trocar 19, the cannula 20 may have a relatively large diameter such as 36 Fr. which is suitable for introducing larger instruments such as a pair of graspers 22.

The catheter 12 is representative of may surgical instruments which must be introduced through the access device 10, in order to perform a particular function within the cavity 14. These instrument typically include an elongate tube or shaft 23 which extends distally of a handle or actuating mechanism, shown generally at 25. In order to reach a particular location within the cavity 14, it may be desirable to provide the shaft 23 with one or more bends, such as the bend 27 illustrated in FIG. 3. It is the bend 27 and the configuration of the access device 10 which facilitates passage of the bend 27, that is of particular interest to the present invention.

A discussion of a typical laparoscopic procedure will be helpful in appreciating the requirements for the bend 27 and the need to pass the catheter 12 through the introducer 18. By way of example, a cholangiography procedure is disclosed in considerable detail in applicant's co-pending application Ser. No. 664,067, referred to above. In this surgical operation it is desirable to introduced radiopaque dye into the cystic duct which attaches the gall bladder to the common bile duct. Using radiography, a picture of this dye will indicated whether there are any gall stones in these ducts.

Unfortunately, the cystic duct cannot be easily accessed by a straight instrument. As illustrated in FIG. 1, the body of a normal patient 13 includes a relatively large liver 30 which extends over a relatively small gall bladder 32. In its normal state the gall bladder 32 is disposed beneath and behind the liver 30, and is relatively inaccessible through the abdominal wall 16 at least from the operative site A. Connected to the gall bladder 32 is a cystic duct 34 which extends to a common bile duct 36.

It is the purpose of the cholangiography procedure to introduce saline and dye 38 through a flexible tube 41 which is connected to the proximal end of the catheter 12. Initially the introducer 18 is inserted through the wall 16 using a needle 41 which is then removed to clear the lumen by the cannula 20. Then by appropriately manipulating the handle or actuator 25, the distal tip of the shaft 23 can be moved through the introducer 18 at a first operative site A, and into a small incision in the cystic duct 34. In this position, the dye 38 is released to flow into the cystic duct 34 and the common bile duct 36.

Due to the inaccessibility of the gall bladder 32 and the cystic duct 34, this procedure is commonly performed by inserting the graspers 22 through a second access device, such as the trocar 19, at a second operative site designated generally by the reference letter B. The graspers 22 are used to engage the gall bladder 32 and to draw it into an upwardly extending, stretched configuration as illustrated by the solid lines in FIG. 2. Even though the cystic duct 34 is more available in this stretched state, access to the duct is greatly facilitated by providing the bend 27 in the catheter shaft 23.

Although the surgical instrument, such as the catheter 12, is discussed with reference to a cholangiography procedure, it will be apparent that this instrument is merely representative of many elongate surgical instruments and devices which can benefit from a bend in an elongate shaft. As noted, these bends are particularly useful where a specific location in a cavity, such as the abdominal cavity 14, must be reached through a single insertion site in the barrier or wall 16.

The operative sites A and B are chosen for a particular procedure as a site of compromise for all of the instruments which must introduced through that site. Given the compromised location of the fixed site, it becomes increasingly advantageous to provide an instrument with one or more bends in order to accommodate its individual purpose.

Instruments such as scissors, graspers, staplers, and the like, may equally benefit from having a bend along an elongate shaft. Other passages and cavities, which may be of interest to a particular instrument and access device, might include the thoracic cavity, the bladder and the like.

With further reference to FIG. 3, it will be apparent that the shaft 23 of the instrument 12 includes a primary proximal portion 61 which extends along an axis 63 and a secondary distal portion which extends along an axis 67. The axes 63 and 67 extend along straight lines which intersect and define a plane as shown by the line 70 in FIG. 4a.

The hub 21 includes a central bore 53, the size of which is limited by the fixed diameter of a Luer fitting 52. This bore 53 extends distally of the hub 21 and terminates at a conical surface 54 which is inclined radially inwardly to the diameter of the lumen in the cannula 20.

The size of the introducer 18 may be dependent upon considerations in addition to those relating to the size or configuration of the instrument 12. For example, the cannula 20 is preferably provided with a minimum outside diameter in order to reduce any trauma to the patient 13. In order to provide the cannula 20 with a maximum inside diameter, the walls of the cannula are typically quite thin and are formed from a flexible material such as Teflon ®, a registered trademark of E. I. DuPont de Nemours.

The size of the hub 21 is dictated primarily by the desirability of providing the Luer fitting 52 at the proximal end of the hub 21. This can generally be accommodated and still provide a bore within the hub 21 which is larger in diameter than the lumen in the cannula 21.

In accordance with the present invention, the hub is formed from a flexible material such as a polyurethane blend which permits the hub 21 to bend along progressive positions as the bend 27 moves through the introducer 18. This is not merely a matter of providing a rigid hub 21 with a bend corresponding to the bend in the shaft 23. Rather, the hub 21 must be formed from a low durometer material which will produce a bend which progresses along the hub 21 as the shaft 23 is inserted through the introducer 18. This progression is illustrated in the progressive FIGS. 5a-5d.

In a preferred method for inserting the bend 27 of the shaft 23 through the introducer 18, an initial step is to place the distal portion 65 into the bore 53 until the distal tip 68 contacts the conical surface 54. Further distal movement of the instrument 12 will funnel the tip 68 along the surface 54 until it moves into the lumen of the cannula 20.

Further proximal insertion of the instrument 12 will ultimately bring the bend 27 into contact with the proximal portions of the hub 21. At this point, the hub 21 will begin to flex. The degree of flexure will depend upon the difference in diameter between the shaft 23 and the bore 53. If these diameters are exactly equal, than the degree of flexure of the hub 21 will be equal to the angle of the bend 27. If the diameter of the bore 53 is greater than the shaft, as will typically be the case, the degree of flexure of the hub will be less than the angle of the bend 27. This flexure will initially occur at the proximal end of the hub 21 as illustrated in FIG. 5b.

Further movement of the instrument 12 into the hub 21 may be facilitated by rotating the shaft 23 in the plane 70 (FIG. 3) as shown by the arrow 58. As the bend 27 moves through the hub 21, the point of flexure will also progress along the hub. At some point, depending on the length of the secondary portion 65 of the shaft 23, the distal tip 68 will pass into the cannula 20. This may cause the cannula to bend slightly with respect to the hub 21 as illustrated in FIG. 5c. Ultimately, the secondary portion 65 of the shaft 23 will be disposed entirely within the cannula 20 as the bend 27 clears the hub 21. At this point, illustrated in FIG. 5d, the hub will return to its normal straight configuration in alignment with the primary portion 61 of the shaft 23. When the bend 27 of the shaft 23 has passed entirely through the cannula 20, the introducer 18 will return to its normal straight configuration.

Removal of the instrument 12 reverses the steps as the bend 27 first contacts the distal end of the cannula 20 and moves progressively proximally through the cannula 20 and the hub 21 to clear the introducer 18.

With the disclosure of a flexible hub 21, it will now be apparent that surgical instruments can be configured with shafts 23 having a variety of shapes. Multiple bends or curves, even spirals, can be accommodated by the introducer of the present invention.

This concept is equally applicable to the trocar 19 which, by way of comparison, is larger than the introducer 18 and adapted to accommodate larger and more complex instruments such as the graspers 22. As illustrated in FIG. 6, the trocar 19 also includes a cannula 74 and a housing 76 which is similar in some respects to the hub 21. The trocar 19 may be of the type disclosed in U.S. Pat. No. 4,654,030 which issued to Moll. However, in accordance with this invention, at least a portion of the walls of the housing 76 are formed from a flexible material in order to facilitate the passage of instruments having irregular shaft configurations.

In the case of both the introducer 18 and the trocar 19, the hub 21 and housing 76 respectively, can be formed from any flexible material which is suitable for use in a surgical environment. As used herein, the word "flexible" means that the material and the configuration of the access device is such that the hub 21 or housing 76 as well as the associated cannula can change from a normally straight configuration which would not permit the passage of a bent shaft to a progressively bendable configuration which will permit the passage of a bent shaft. As noted, this flexibility is a function of the material as well as the wall thickness and general configuration of the access device.

With respect to materials, it has been found that a blend of polyvinylchloride and polyurethane is particularly advantageous. In this blend, a relative increase in the amount of polyurethane provides a corresponding increase in flexibility. Various blends of these materials are commonly available and differ generally in their flexibility as measured by their Shore A Hardness. Depending on the thickness of the walls associated with the introducer 18 and the trocar 19, a Shore A Hardness less than 100 is preferred. In a preferred embodiment the blend of polyvinylchloride and polyurethane is sold under the trademark VYTHENE ® and has a Shore A Hardness of 68.

In this embodiment, the hub 21 has a wall thickness of about 0.030 inches. It will be understood that as the wall thickness decreases, the flexibility of the hub increases. In access devices having relatively thin walls, materials which are generally thought to be more rigid may be applicable to the concept. In such an embodiment, a material such as polytetrafluoroethylene may additionally provide a lubricous surface at the bore 53. Such as surface would tend to decrease the friction forces which might otherwise be associated with forcing a bent instrument through a narrow passage. A lubricous surface might also be provide in the form of a coating of silicone.

The configuration of the hub 21 or housing 76 may also affect the flexibility of the structure. Adding axial ribs along the hub 21 or housing 76 would of course reduce the flexibility of the structure.

With the numerous possibilities and variations in this concept, one should not determine the scope of this invention with reference merely to the embodiments illustrated and disclosed; rather, specific attention should be directed to the following claims.

I claim:

1. An access device adapted to facilitate introduction of an instrument into a body cavity, the instrument having an elongate shaft and a bend in the shaft, the device including:
   a cannula having a proximal end and a distal end, and portions defining a channel extending along an axis between the proximal end and the distal end, the cannula being adapted for insertion into the body cavity with the distal end of the cannula disposed inside the cavity and the proximal end of the cannula disposed outside the cavity;

a hub disposed at the proximal end of the cannula, the hub having a wall with an inner surface defining an axial bore communicating with the channel of the cannula and the hub being formed of a resilient material and having properties for being progressively bent along the axis of the hub to permit insertion of the bend of the rigid instrument through the access device.

2. The device recited in claim 1 wherein the resilient material of the hub has a Shore A hardness not greater than 100.

3. The device recited in claim 2 wherein the Shore A hardness is in a range between 50 and 75.

4. The device recited in claim 3 wherein the Shore A hardness is about 68.

5. A method for inserting an instrument into a body cavity, the instrument having a rigid elongate shaft and a bend in the shaft, the method including the steps of:

providing an access device having an elongate cannula with a channel and a flexible hub having a bore extending into the channel;

inserting the rigid shaft of the instrument into the hub up to the bend in the shaft;

moving the bend in the shaft progressively through the bore of the hub and the channel of the cannula; and during the moving step progressively bending the hub to facilitate passage of the bend of the shaft through the bore of the hub.

6. The method recited in claim 5 wherein the bend in the shaft of the instrument is characterized by the general intersection of a primary section disposed along a primary axis of the instrument and a secondary section disposed along a secondary axis of the instrument, and the bending step further comprises the steps of:

moving the secondary section of the shaft into the bore of the hub;

rotating the shaft in a particular plane including the primary axis and the secondary axis; and during the rotating step, advancing the bend of the shaft through the bore of the hub.

7. A combination for performing a surgical function in a body cavity defined by a body wall of a patient, comprising:

an instrument adapted to perform the surgical function in the body cavity;

a rigid shaft included in the instrument and having a length sufficient to reach the body cavity from a location exterior of the body wall, the shaft including a first portion, a second portion, and a bend disposed between the first portion and the second portion of the shaft;

access means for facilitating passage of the secondary section of the instrument into the body cavity, the access means including a cannula extending across the body wall of the patient and a hub disposed exteriorly of the body wall of the patient;

portions of the hub defining a bore extending along an axis through the hub and communicating with the cannula; and the hub being formed of a resilient material and having properties for being progressively bent along the axis of the hub to permit insertion of the bend of the rigid shaft through the access means.

8. The combination recited in claim 7 wherein the resilient material of the hub has a Shore A hardness in a range between 50 and 75.

9. The combination recited in claim 7 wherein the resilient material comprises VYTHENE®.

10. An access device adapted to facilitate introduction of an instrument into a body cavity, the instrument having an elongate shaft and a bend in the shaft, the device including:

a cannula having a proximal end and a distal end, and portions defining a channel extending along an axis between the proximal end and the distal end, the cannula being adapted for insertion into the body cavity with the distal end of the cannula disposed generally inside the cavity and the proximal end of the cannula disposed generally outside the cavity;

a hub disposed at the proximal end of the cannula, the hub having a wall with an inner surface defining an axial bore communicating with the channel of the cannula; and the hub being formed from VYTHENE® and having properties for being progressively bent along the axis of the hub to permit insertion of the bend of the rigid instrument through the access device.

11. A method for inserting an instrument into a body cavity, the instrument having a rigid elongate shaft and a bend in the shaft characterized by the general intersection of a primary section disposed along a primary axis of the instrument and a secondary section disposed along a secondary axis of the instrument, the method including the steps of:

providing an access device having an elongate cannula with a channel and a flexible hub having a bore extending into the channel;

inserting the rigid shaft of the instrument into the hube up to the bend in the shaft;

moving the secondary section of the shaft into the bore of the hub;

rotating the shaft in a particular plane including the primary axis and the secondary axis; and during the rotating step, advancing the bend of the shaft through the bore of the hub.

* * * * *